US012642641B2

(12) United States Patent
Yoshimori et al.

(10) Patent No.: US 12,642,641 B2
(45) Date of Patent: Jun. 2, 2026

(54) INDWELLING DEVICE

(71) Applicant: SB-KAWASUMI LABORATORIES, INC., Kawasaki (JP)

(72) Inventors: Takashi Yoshimori, Kawasaki (JP); Tomohiro Emi, Kawasaki (JP); Naoaki Yamamoto, Kawasaki (JP)

(73) Assignee: SB-KAWASUMI LABORATORIES, INC., Kawasaki (JP)

( * ) Notice: Subject to any disclaimer, the term of this patent is extended or adjusted under 35 U.S.C. 154(b) by 852 days.

(21) Appl. No.: 17/913,335

(22) PCT Filed: Mar. 26, 2021

(86) PCT No.: PCT/JP2021/013026
§ 371 (c)(1),
(2) Date: Sep. 21, 2022

(87) PCT Pub. No.: WO2021/193955
PCT Pub. Date: Sep. 30, 2021

(65) Prior Publication Data
US 2023/0123047 A1 Apr. 20, 2023

(30) Foreign Application Priority Data

Mar. 27, 2020 (JP) ................................. 2020-057471

(51) Int. Cl.
*A61F 2/07* (2013.01)
(52) U.S. Cl.
CPC .......... *A61F 2/07* (2013.01); *A61F 2002/077* (2013.01)

(58) Field of Classification Search
CPC ........ A61F 2002/077; A61F 2002/9665; A61F 2/966; A61F 2002/9511; A61F 2/95
See application file for complete search history.

(56) References Cited

U.S. PATENT DOCUMENTS

| | | | |
|---|---|---|---|
| 5,843,162 | A | 12/1998 | Inoue |
| 6,371,979 | B1 | 4/2002 | Beyar et al. |
| 9,456,913 | B2 | 10/2016 | Melsheimer |
| 2003/0014103 | A1 | 1/2003 | Inoue |
| 2005/0090834 | A1 | 4/2005 | Chiang et al. |
| 2007/0016281 | A1 | 1/2007 | Melsheimer |
| 2008/0039927 | A1 | 2/2008 | Barr |

(Continued)

FOREIGN PATENT DOCUMENTS

| | | |
|---|---|---|
| JP | 2019-118809 | 7/2019 |
| WO | WO 2019/181821 | 3/2021 |

OTHER PUBLICATIONS

Notice of Reasons of Refusal issued Nov. 11, 2025, in corresponding Japanese patent application No. 1 2024-164293 .

*Primary Examiner* — Andrew Restaino
(74) *Attorney, Agent, or Firm* — Womble Bond Dickinson (US) LLP

(57) ABSTRACT

A shaft-shaped member 30 of an indwelling device 1 has an engaged portion 33 with which an engaging portion 15 of a tubular treatment device 10 engages, and a restriction portion 34 that restricts expansion of the engaging portion 15 engaged with the engaged portion 33 in a radial direction in cooperation with a linear member 36. The restriction portion 34 releases restriction on the expansion of the engaging portion 15 in the radial direction by releasing winding of the linear member 36 around the engaging portion 15.

3 Claims, 7 Drawing Sheets

(56) References Cited

U.S. PATENT DOCUMENTS

| | | | | |
|---|---|---|---|---|
| 2008/0114442 | A1 | 5/2008 | Mitchell et al. | |
| 2008/0221666 | A1* | 9/2008 | Licata | A61F 2/95 |
| | | | | 623/1.22 |
| 2009/0082842 | A1* | 3/2009 | Glynn | A61F 2/962 |
| | | | | 623/1.11 |
| 2009/0082844 | A1* | 3/2009 | Zacharias | A61F 2/915 |
| | | | | 623/1.13 |
| 2010/0016943 | A1* | 1/2010 | Chobotov | A61F 2/07 |
| | | | | 623/1.13 |
| 2010/0249896 | A1* | 9/2010 | Sugimoto | A61F 2/95 |
| | | | | 623/1.34 |
| 2014/0180386 | A1 | 6/2014 | Huser | |
| 2014/0236278 | A1 | 8/2014 | Argentine et al. | |
| 2016/0250051 | A1 | 9/2016 | Lim et al. | |
| 2021/0220013 | A1* | 7/2021 | Libarnes | A61B 17/12022 |

* cited by examiner (a)

(b)

(c)

(a)

(b)

INDWELLING DEVICE

CROSS-REFERENCE TO RELATED APPLICATIONS

This application is a national stage filing under 35 U.S.C. 371 of PCT/JP2021/013026, filed Mar. 26, 2021, which International Application was published by the International Bureau in English on Sep. 30, 2021, as WO 2021/193955, and application claims priority from Japanese Application No. 2020-057471, filed on Mar. 27, 2020, which applications are hereby incorporated by reference in their entirety in this application.

TECHNICAL FIELD

The present invention relates to an indwelling device.

BACKGROUND ART

In the related art, a tubular treatment device such as a stent graft used for treating a lump appearing on a vascular wall is known. Various proposals have been made for an indwelling device for delivering the tubular treatment device to indwell an affected area (For example, refer to Patent Documents 1 to 3). In general, the indwelling device delivers the tubular treatment device to the affected area in a state of being contracted in a radial direction, and expands the tubular treatment device in the affected area in the radial direction so that the tubular treatment device indwells the affected area.

One of the indwelling devices in the related art enables indwelling of a so-called tip posterior opening type tubular treatment device. For example, this type of the indwelling device has a tip chip capable of accommodating an arm-shaped portion provided in an open end of a main body portion of the tubular treatment device (for example, refer to Patent Document 1). In the above-described indwelling device, the tubular treatment device is delivered to the affected area while the arm-shaped portion is accommodated in the tip chip, and the main body portion is expanded in the affected area. Thereafter, the arm-shaped portion is released from the tip chip to bring the tubular treatment device into contact with the vascular wall.

PRIOR ART DOCUMENT

Patent Document

[Patent Document 1] Japanese Patent No. 5408866
[Patent Document 2] Japanese Patent No. 4928449
[Patent Document 3] Japanese Patent No. 6261619

SUMMARY OF INVENTION

Technical Problem

As a mechanism for releasing the arm-shaped portion accommodated in the tip chip, the above-described indwelling device has two shafts including a shaft connected to the tip chip accommodating the arm-shaped portion and a shaft holding the arm-shaped portion to be relatively movable with respect to the tip chip. Therefore, the above-described indwelling device has a complicated structure and a large number of components. In addition, the two shafts in the above-described indwelling device have a double structure in which the other shaft is inserted into a hollow portion of one shaft. Therefore, in the above-described indwelling device, a diameter of a sheath accommodating the tubular treatment device also increases.

Therefore, the present invention is made in view of the above-described problem, and an object of the present invention is to provide an indwelling device which can reduce a diameter of a sheath for accommodating a tubular treatment device and can simplify a device structure.

Solution to Problem

One aspect of the present invention is an indwelling device that causes a tubular treatment device expandable in a radial direction to indwell a living body lumen. The indwelling device includes a sheath capable of accommodating the tubular treatment device, and an elongated shaft-shaped member configured to be movable forward and rearward inside the sheath along an axial direction of the sheath. The shaft-shaped member has an engaged portion with which an engaging portion of the tubular treatment device engages, and a restriction portion that holds a linear member wound around the engaging portion engaged with the engaged portion and restricts expansion of the engaging portion in the radial direction by using the linear member. The restriction portion releases restriction on the expansion of the engaging portion in the radial direction by releasing winding of the linear member around the engaging portion.

Advantageous Effects of Invention

According to the present invention, it is possible to reduce a diameter of a sheath for accommodating a tubular treatment device and to simplify a device structure.

DESCRIPTION OF EMBODIMENTS

Hereinafter, a configuration example of an indwelling device and a tubular treatment device according to an embodiment of the present invention will be described with reference to the drawings.

Figure 1:
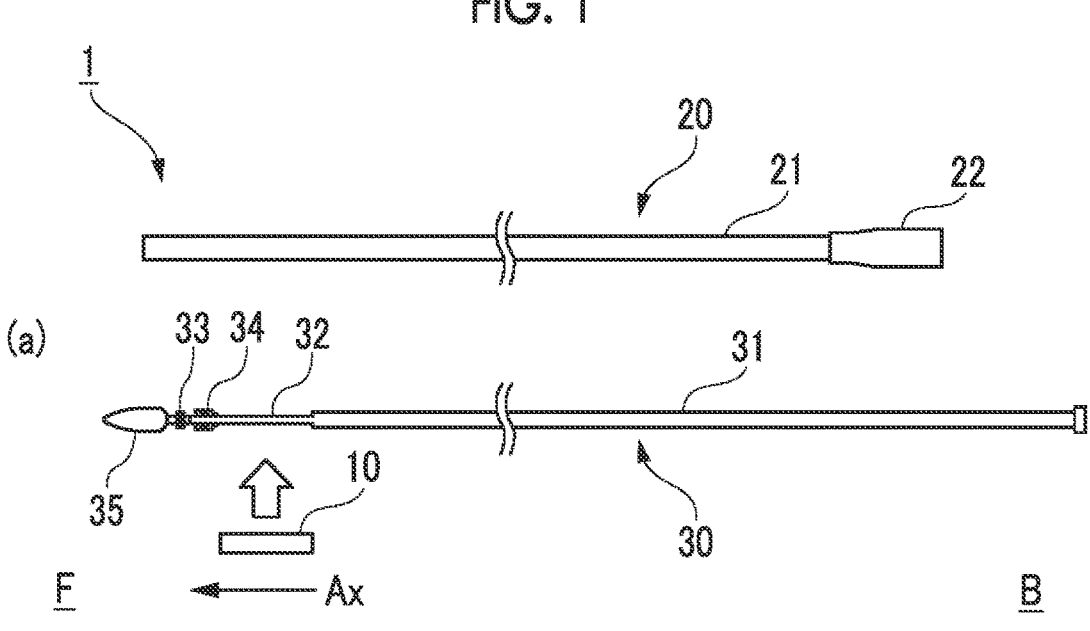
FIG. 1(a) is an exploded view of an indwelling device of the present embodiment.
FIG. 1(b) is a view illustrating an assembled state of the indwelling device of the present embodiment.
FIG. 1(c) is a view illustrating the vicinity of an opening portion on one side in a stent graft of the present embodiment.
Figure 1:
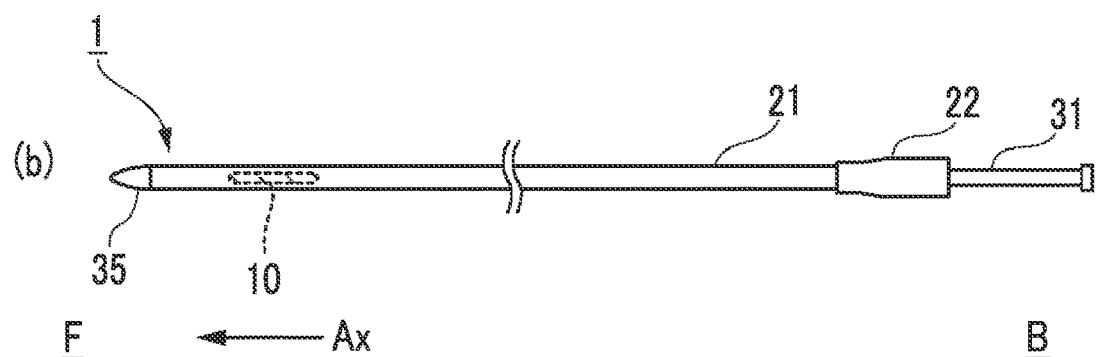
Figure 1:
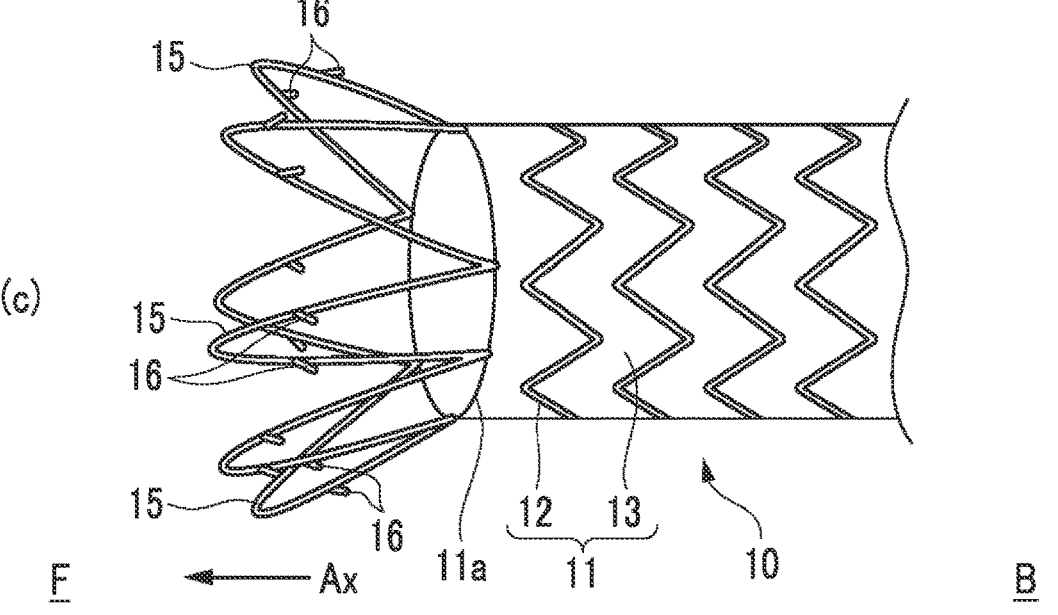

FIG. 1(*a*) is an exploded view of an indwelling device 1 of the present embodiment, and FIG. 1(*b*) is a view illustrating an assembled state of the indwelling device 1 of the present embodiment. FIG. 1(*c*) is a view illustrating the vicinity of an opening portion on one side in a stent graft 10 of the present embodiment.

A shape or a dimension of each portion in the drawings is schematically illustrated, and does not indicate an actual shape or an actual dimension. In the drawings, an axial direction Ax of the indwelling device and a tubular treatment device are indicated by arrows when necessary. In addition, a direction substantially orthogonal to the axial direction Ax is defined as a radial direction. When necessary, one side of the indwelling device and the tubular treatment device is indicated by a reference numeral F, and the other side is indicated by a reference numeral B in the drawings.

First, a configuration of the stent graft 10 of the present embodiment will be described.

The stent graft 10 is an example of the tubular treatment device, and is caused to indwell a lesion site such as a stenosis site and an occlusion site in a living body lumen, and is applied to enlarge the lesion sites. The stent graft 10 is caused to indwell at a predetermined position of a blood vessel (for example, a lesion site where a lump appears in the blood vessel) which is an example of a living body lumen by using the indwelling device.

Figure 3:
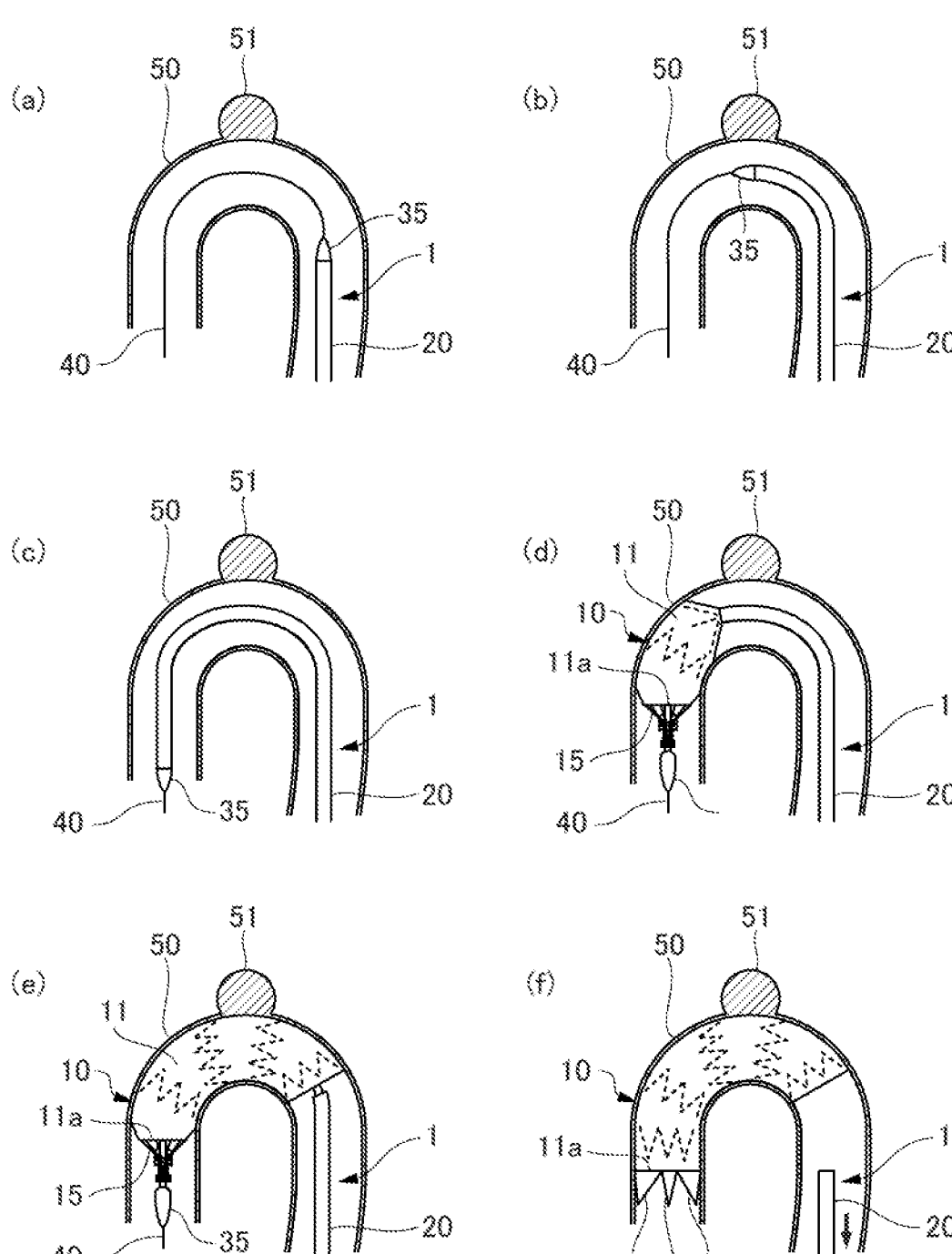
FIGS. 3(a) to 3(f) are views illustrating a procedure for indwelling of the stent graft by using the indwelling device.

The stent graft 10 has a so-called self-expandable configuration in which a shape in an expanded state is memorized. The stent graft 10 is accommodated in a tubular sheath 20 of the indwelling device 1, and is introduced into the blood vessel in a state of being contracted inward in the radial direction. The stent graft 10 is released from the sheath 20 after being delivered to the predetermined position in the blood vessel, and expands outward in the radial direction. As illustrated in FIG. 3(*f*) to be described later, the expanded stent graft 10 is caused to indwell the blood vessel in a state of being in close contact with an inner wall of the blood vessel.

An overall shape of the stent graft 10 may be a linear shape, or may be a curved shape corresponding to a shape of the blood vessel of a patient. That is, the stent graft 10 may be curved in advance on an assumption of an indwelling location before indwelling of the stent graft 10, or may be curved along the shape of the blood vessel after indwelling of the stent graft 10.

The stent graft 10 includes a main body portion 11 formed in a tubular shape in which one side and the other side in the axial direction Ax communicate with each other. As illustrated in FIG. 1(*c*), the main body portion 11 has a skeleton portion 12 and a membrane portion 13 fixed to the skeleton portion 12. An internal space of the main body portion 11 forms a flow path through which a blood flow of the patient can pass when the stent graft 10 is caused to indwell the blood vessel.

For example, the skeleton portion 12 is formed by spirally winding a thin metal wire (wire rod). For example, the skeleton portion 12 is formed by spirally winding the thin metal wire while folding the thin metal wire in zigzags so that a peak portion and a valley portion are alternately formed. The skeleton portion 12 is configured to be deformable so that the skeleton portion 12 is self-expandable from a contracted state of being contracted inward in the radial direction to an expanded state of being expanded outward in the radial direction.

For example, a material forming the thin metal wire of the skeleton portion 12 includes known metal or metal alloy represented by Ni—Ti alloy (Nitinol), cobalt-chromium alloy, titanium alloy, and stainless steel. When the Ni—Ti alloy is used as the material of the skeleton portion 12, a shape of the skeleton portion 12 in an expanded state can be memorized in the skeleton portion 12 by performing a predetermined heat treatment after the skeleton portion 12 is adjusted to have the shape in the expanded state. The skeleton portion 12 may be formed of a material other than metal (for example, ceramic or a resin).

The membrane portion 13 is a tubular flexible membrane body that forms the above-described flow path, and is attached to the skeleton portion 12 to close a gap portion of the skeleton portion 12. For example, a material for forming the membrane portion 13 includes a fluororesin such as polytetrafluoroethylene (PTFE) and a polyester resin such as polyethylene terephthalate.

As an example of an engaging portion, a bare portion 15 formed of a metal skeleton is provided in an open end 11*a* on one side of the main body portion 11. The bare portion 15 protrudes from the open end 11*a* of the main body portion 11 toward one side in the axial direction Ax. The bare portion 15 has a function of generating friction with an inner wall of the blood vessel when the stent graft 10 is caused to indwell the blood vessel and preventing misalignment (migration) of the stent graft 10.

In addition, the bare portion 15 is provided with a fixing pin (also referred to as a barb) 16 protruding outward in the radial direction. The fixing pin 16 has a function of assisting the bare portion 15 to be fixed to the blood vessel by being caught on the inner wall of the blood vessel.

Next, a configuration example of the indwelling device in the present embodiment will be described.

As illustrated in FIGS. 1(*a*) and 1(*b*), the indwelling device 1 includes a tubular sheath 20 and a tubular shaft 30 disposed inside the sheath 20.

The sheath 20 can internally accommodate the stent graft 10 in a contracted state. The sheath 20 has a sheath main body portion 21 and a hub 22 provided in an end portion on the other side of the sheath main body portion 21. The hub 22 has a nut (not illustrated) for fixing the sheath 20 to the shaft 30, and an operating member (not illustrated) for operating a linear member 36 (to be described later).

The sheath main body portion 21 is a tubular body formed of a flexible material. As the material of the sheath main body portion 21, for example, a biocompatible synthetic resin (elastomer) selected from a fluororesin, a polyamide resin, a polyethylene resin, and a polyvinyl chloride resin, a resin compound in which other materials are mixed with the synthetic resins, a multilayer structure formed of the synthetic resins, and a composite of the synthetic resins and a metal wire may be used.

The shaft 30 is a shaft-shaped member longer than the sheath 20, and is configured to be movable forward and rearward along the axial direction Ax. The shaft 30 has a shaft main body portion 31 and a shaft small diameter portion 32 formed on one side of the shaft main body portion 31. As the material of the shaft 30, for example, various materials having proper hardness and flexibility, such as a resin (plastic and elastomer) and metal.

The shaft small diameter portion 32 is coaxial with the shaft main body portion 31, and has a smaller diameter than the shaft main body portion 31. In the indwelling device 1, the stent graft 10 is accommodated in a space formed between an outer periphery of the shaft small diameter portion 32 and an inner periphery of the sheath main body portion 21. In addition, a hole (not illustrated) for inserting a guide wire 40 (to be described later) is formed in the shaft main body portion 31 and the shaft small diameter portion 32 30 of the shaft 30 along the axial direction Ax.

In addition, a tip chip 35 that closes an end portion opening on one side of the sheath 20 is attached to an end portion on one side of the shaft small diameter portion 32.

Figure 2:
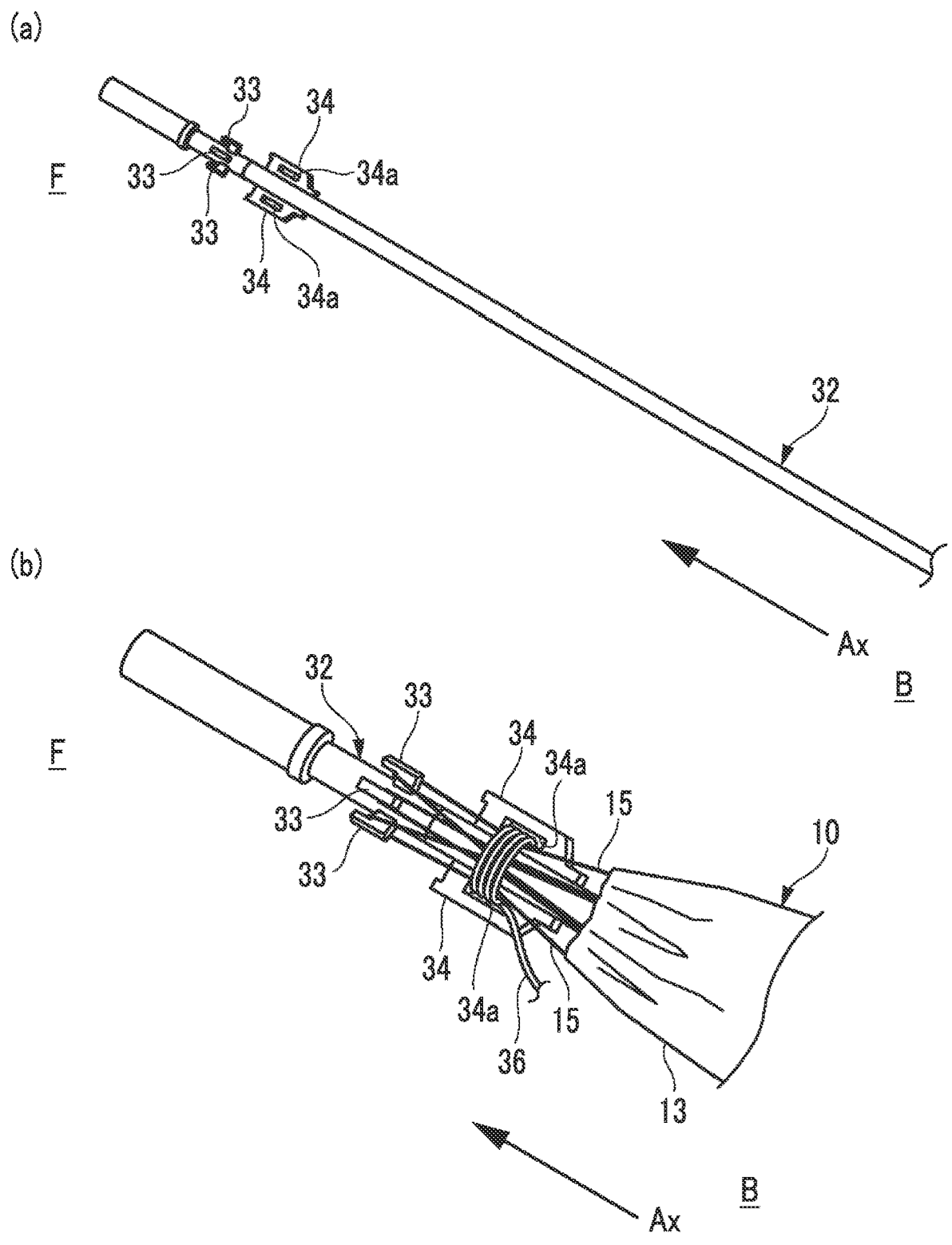
FIG. 2(a) is a perspective view illustrating a configuration example in the vicinity of a tip portion of a shaft small diameter portion.
FIG. 2(b) is a view illustrating a state where the stent graft is attached to the shaft small diameter portion.

FIG. 2(*a*) is a perspective view illustrating a configuration example in the vicinity of a tip portion of the shaft small diameter portion 32. FIG. 2(*b*) is a view illustrating a state where the stent graft 10 is attached to the shaft small diameter portion 32. In FIGS. 2(*a*) and 2(*b*), the tip chip 35 is omitted in the illustration.

The shaft small diameter portion 32 has a hook piece 33 and a linear member holder 34 in this order from an end portion on one side.

The hook piece 33 is an example of an engaged portion, and is formed in a shape in which a base end side rises from the shaft small diameter portion 32 in the radial direction, and a tip portion thereof is bent and protrudes to one side of the shaft small diameter portion 32. A plurality of the hook pieces 33 are provided at an interval in a circumferential direction of the shaft small diameter portion 32. As illustrated in FIG. 2(*b*), an end portion of the bare portion 15 can be hooked on and engage with each of the hook pieces 33.

The linear member holder 34 is a flat plate-shaped small piece that rises in the radial direction from the shaft small diameter portion 32 and extends along the axial direction Ax. In the linear member holder 34, a holding hole 34*a* into which the linear member 36 is inserted in the circumferential direction is opened. The linear member 36 is formed of a material having predetermined strength and rigidity, and for example, a suture such as nylon fiber and fluorine fiber, a nickel-titanium alloy, a stainless steel-made thin metal wire, or a resin-made string-shaped member can be applied.

In an example in FIG. 2, two linear member holders 34 are disposed with an interval of 180 degrees in the shaft small diameter portion 32. The number of the linear member holders 34 in the shaft small diameter portion 32 is not limited to the above-described example. The number may be one, or may be three or more.

As illustrated in FIG. 2(*b*), when the stent graft 10 is attached to the shaft small diameter portion 32, the bare portion 15 of the stent graft 10 is hooked on and engaged with the hook piece 33 of the shaft small diameter portion 32. Then, the linear member 36 is wound in the circumferential direction from the outside of the bare portion 15 engaged with the hook piece 33. Since the linear member 36 is wound, outward expansion of the bare portion 15 in the radial direction is restrained and restricted by the linear member 36, and an end portion on one side of the stent graft 10 is fixed to the shaft small diameter portion 32.

The above-described linear member 36 is wound across the plurality of bare portions 15 in the circumferential direction through the holding hole 34*a* of the linear member holder 34. A force outward in the radial direction which is generated by a reaction force from the bare portion 15 acts on the linear member 36 that winds the bare portion 15. However, since the linear member 36 passes through the holding hole 34*a* of the linear member holder 34, the linear member 36 is held by the linear member holder 34. In this manner, outward displacement of the linear member 36 in the radial direction is restricted, and the wound state of the linear member 36 in the bare portion 15 can be easily maintained.

In this way, the linear member holder 34 functions as a restriction portion that restricts expansion of the bare portion 15 engaged with the hook piece 33 in the radial direction in cooperation with the linear member 36.

In addition, the other side of the linear member 36 passes through the inside of the sheath 20, and is connected to an operating member of the hub 22 provided in an end portion on the other side of the sheath 20. Since the operating member of the hub 22 is operated, the linear member 36 can be pulled out to the other side. When the linear member 36 is pulled out to the other side, winding of the linear member 36 is released, and the bare portion 15 is brought into an expandable state in the radial direction.

Here, a procedure for indwelling of the stent graft 10 in a blood vessel 50 by using the indwelling device will be described with reference to FIGS. 3(*a*) to 3(*f*). An example in FIG. 3 illustrates a case where the stent graft 10 is caused to indwell a lesion site where a lump 51 appears in the curved blood vessel 50. A left side in each drawing of FIG. 3 corresponds to one side, and a right side in each drawing of FIG. 3 corresponds to the other side.

First, the guide wire 40 is disposed inside the blood vessel 50 to pass through the lesion site where the lump 51 appears. Then, with respect to the indwelling device 1 accommodating the stent graft 10 in a contracted state, the guide wire 40 is inserted into the indwelling device 1 from an end portion on one side of the indwelling device 1. Thereafter, as illustrated in FIGS. 3(*a*) to 3(*c*), the indwelling device 1 is moved forward into the blood vessel from the other side toward one side along the guide wire 40 so that an end portion on one side of the indwelling device 1 passes through the lesion site where the lump 51 appears.

Next, as illustrated in FIGS. 3(*d*) to 3(*e*), in the indwelling device 1, the sheath 20 is moved toward the other side to be pulled out while holding a position of the shaft 30 that restrains the bare portion 15 of the stent graft 10. In this case, the stent graft 10 is released from the sheath 20 of the indwelling device 1. The main body portion 11 of the stent graft 10 is released outward from the sheath 20 to self-expand outward in the radial direction. In this manner, the expanded main body portion 11 comes into close contact with an inner wall surface of the blood vessel 50.

FIG. 3(*e*) illustrates a state where the whole stent graft 10 is released from the sheath 20. In the state in FIG. 3(*e*), the stent graft 10 is fixed to the blood vessel to cover the lesion site where the lump 51 appears from the inside of the blood vessel 50.

In stages in FIGS. 3(*a*) to 3(*e*) described above, the linear member 36 is wound around the outside of the bare portion 15 so that expansion of the bare portion 15 in the radial direction is brought into a restricted state.

Thereafter, winding of the linear member 36 is released in the indwelling device 1 so that restriction on the expansion of the bare portion 15 in the radial direction is released. In this case, the bare portions 15 expand outward in the radial direction due to a self-expanding force, and respectively come into contact with an inner wall of the blood vessel 50 (refer to FIG. 3(*f*)). In this manner, the bare portion 15 and the fixing pin 16 cause friction against the inner wall of the blood vessel 50, and misalignment of the stent graft 10 from an indwelling position is prevented.

Thereafter, as illustrated in FIG. 3(*f*), the sheath 20 and the guide wire 40 are pulled out to the other side, and the indwelling device 1 is removed from the inside of the blood vessel. Through the above-described procedure, indwelling of the stent graft 10 is completed.

Hereinafter, an advantageous effect of the indwelling device 1 of the present embodiment will be described.

In the indwelling device 1 of the present embodiment, the shaft small diameter portion 32 of the shaft 30 has the hook piece 33 with which the bare portion 15 of the stent graft 10 engages, and the linear member holder 34. The linear member holder 34 restricts the expansion of the bare portion 15 engaged with the hook piece 33 in the radial direction in cooperation with the linear member 36. In addition, the linear member holder 34 releases the restriction on the expansion of the bare portion 15 in the radial direction by releasing the winding of the linear member 36 around the bare portion 15.

According to the present embodiment, switching from a state where the expansion of the bare portion 15 in the radial direction is restricted to a state where the restriction is released can be performed by operating the linear member 36. That is, in the present embodiment, in order to release the restriction on the expansion of the bare portion 15 in the radial direction, for example, a mechanism having a double structure shaft may not be provided inside the sheath 20. Therefore, a device structure of the indwelling device 1 is simplified. Assembly workability can be improved, and manufacturing costs can be minimized by reducing the number of components.

In addition, according to the present embodiment, the mechanism having the double structure shaft may not be provided inside the sheath 20 as described above. Therefore, an outer diameter of the sheath 20 can be smaller than that of the indwelling device having the double structure shaft. Therefore, in a procedure for indwelling of the stent graft 10, the sheath 20 of the indwelling device 1 can be smoothly introduced into the blood vessel, and invasiveness to a patient's body can be reduced.

In addition, in the indwelling device having the double structure shaft as described above, a double structure portion is less likely to be bent, and is less likely to be introduced into the curved blood vessel. In contrast, the indwelling device 1 of the present embodiment does not have the above-described double structure shaft. Accordingly, the indwelling device 1 is likely to be bent, and can be more easily introduced into the curved blood vessel.

In addition, in the indwelling device having the double structure shaft as described above, for example, when the stent graft 10 is caused to indwell the curved blood vessel, one shaft and the other shaft come into contact with each other while a portion in the circumferential direction is biased due to bending of the whole shaft along the curve of the blood vessel. Consequently, an event may occur in which smooth sliding of both the shaft is hindered. In contrast, the present embodiment does not adopt the double structure shaft, and the bare portion 15 can be expanded in the radial direction by releasing the winding of the linear member 36. Therefore, in the present embodiment, even when the stent graft 10 is caused to indwell the curved blood vessel, the bare portion 15 can be smoothly expanded in the radial direction as in a case where the stent graft 10 is caused to indwell a non-curved blood vessel. Therefore, reliability of the operation of the indwelling device 1 can be improved.

Next, as a modification example of the above-described embodiment, a configuration will be described in which the bare portion 15 is restricted so that the bare portion 15 can be switched from a reduced diameter state to an enlarged diameter state by using two linear members.

Figure 4:
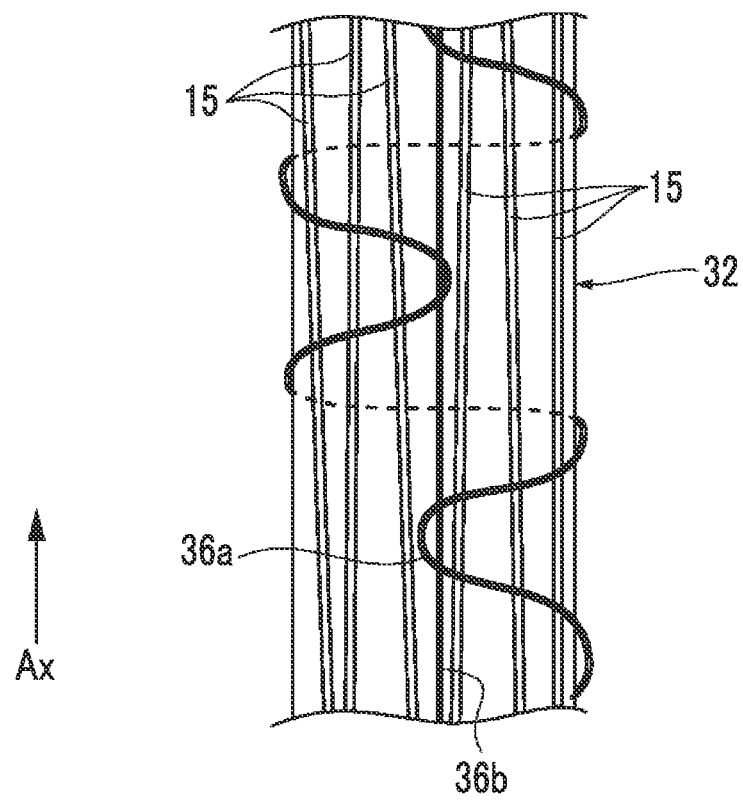
FIG. 4 is a view illustrating a first modification example of restriction of a bare portion by winding a linear member.

FIG. 4 is a view illustrating a first modification example of the restriction of the bare portion 15 by winding the linear member. In the first modification example, the expansion of the bare portion 15 in the radial direction is restricted by the first linear member 36a wound around an outer peripheral surface of the bare portion 15 and the second linear member 36b engaged with the first linear member 36a.

The first linear member 36a is wound around the outer peripheral surface of the bare portion 15 in a mode in which the wound state cannot be held by itself, and is held to be non-detachable by engaging with the second linear member 36b. That is, the second linear member 36b holds the first linear member 36a to be non-detachable from the bare portion 15 and the shaft small diameter portion 32.

Specifically, the first linear member 36a is wound around the outer peripheral surface of the bare portion 15 in the circumferential direction, and is wound in the opposite direction while being bent at each rotation. Bent portions of the first linear member 36a are formed in parallel in the axial direction Ax. On the other hand, the second linear member 36b is disposed along the axial direction Ax by sewing each of the bent portions of the first linear member 36a. That is, the second linear members 36b are respectively inserted into the bent portions of the first linear member 36a. In addition, the other side of the second linear member 36b passes through the inside of the sheath 20, and is connected to the operating member of the hub 22 provided in an end portion on the other side of the sheath 20 so that the second linear member 36b can be pulled out along the axial direction.

In an example in FIG. 4, the first linear member 36a and the second linear member 36b are engaged with each other by winding the first linear member 36a around the second linear member 36b disposed along the axial direction Ax while the bent portion is hooked. In this case, tension is applied by properly pulling both ends of the first linear member 36a. In this manner, the diameter of the bare portion 15 can be reduced.

In addition, the first linear member 36a is held in a wound state by engaging with the second linear member 36b. Therefore, when the first linear member 36a and the second linear member 36b are disengaged from each other by pulling out the second linear member 36b, the first linear member 36a is naturally detached from the shaft small diameter portion 32. In this manner, the restriction on the expansion of the bare portion 15 in the radial direction can be released.

Here, the same as the above-described linear member 36 can be applied to the first linear member 36a and the second linear member 36b. In order to improve slipping performance and easily pull out the second linear member 36b, it is preferable that the first linear member 36a and the second linear member 36b are formed of different materials. In addition, it is preferable that the second linear member 36b is formed of a material having predetermined strength and rigidity, and the first linear member 36a is formed of a material having lower rigidity than the second linear member 36b. For example, a suture thread such as nylon fiber or fluorine fiber or a string-shaped member formed of a resin can be applied to the first linear member 36a, and a nickel-titanium alloy or stainless steel-made thin metal wire can be applied to the second linear member 36b. In addition, the first linear member 36a may be formed in a wide tape shape.

A winding mode of the first linear member 36a in the modification example illustrated in FIG. 4 is an example, and other winding modes may be applied.

Next, a second modification example of the above-described embodiment will be described. In describing the second modification example, the same reference numerals will be assigned to elements the same as those of the above-described embodiment and the first modification example, and any repeated description will be omitted.

As in the first modification example described with reference to FIG. 4, the second modification example has a configuration in which the bare portion 15 is restricted so that the bare portion 15 can be switched from a reduced diameter state to an enlarged diameter state by using two linear members. In the second modification example, the expansion of the bare portion 15 in the radial direction is also restricted by the first linear member 36a wound around the outer peripheral surface of the bare portion 15 and the second linear member 36b engaged with the first linear member 36a.

Although not particularly limited, in the second modification example, the first and second linear members 36a and 36b may also have the configuration the same as the configuration of the first modification example.

Figure 5:
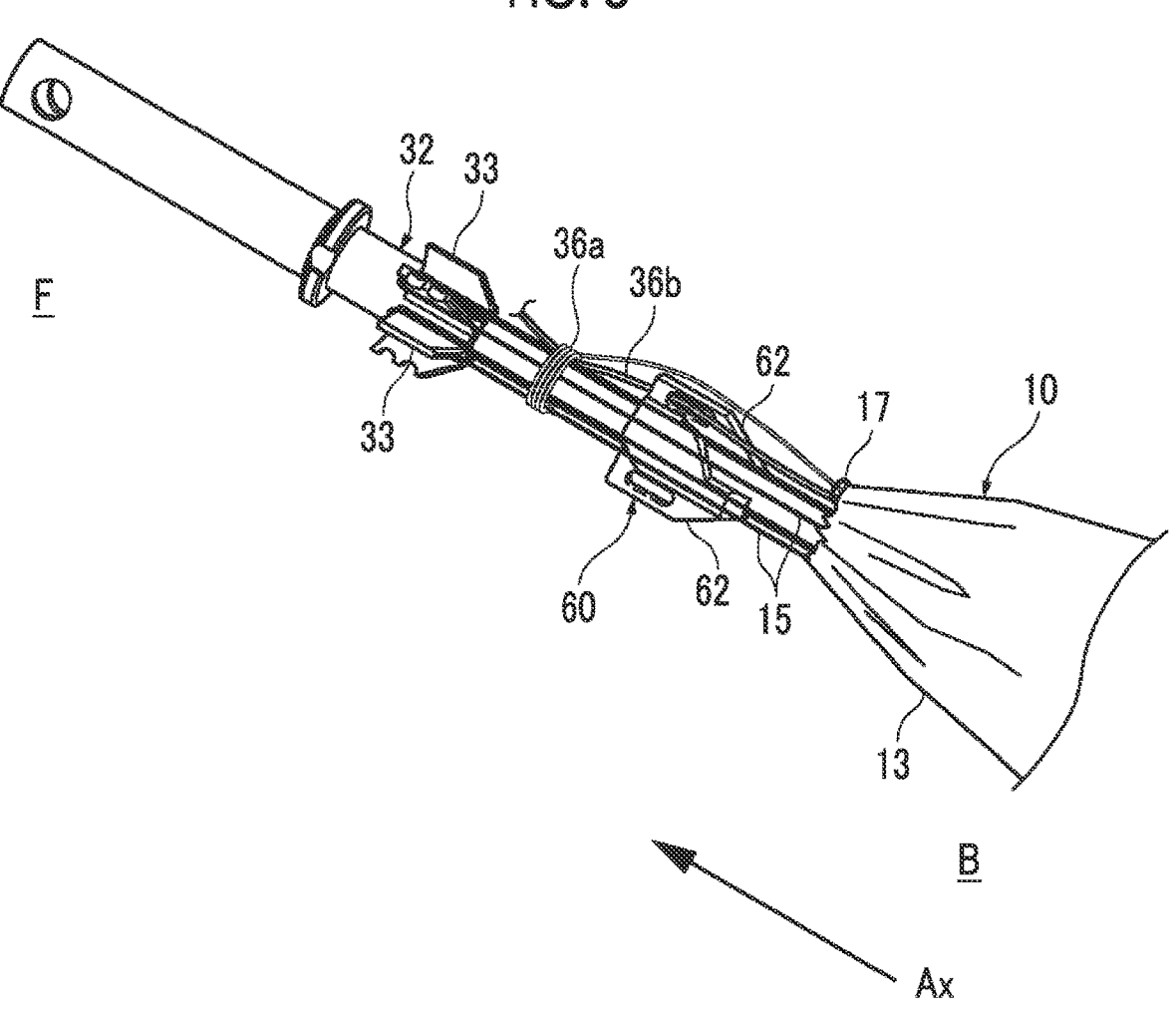
FIG. 5 is a perspective view illustrating a state where a stent graft is attached to a shaft small diameter portion in a second modification example.
Figure 6:
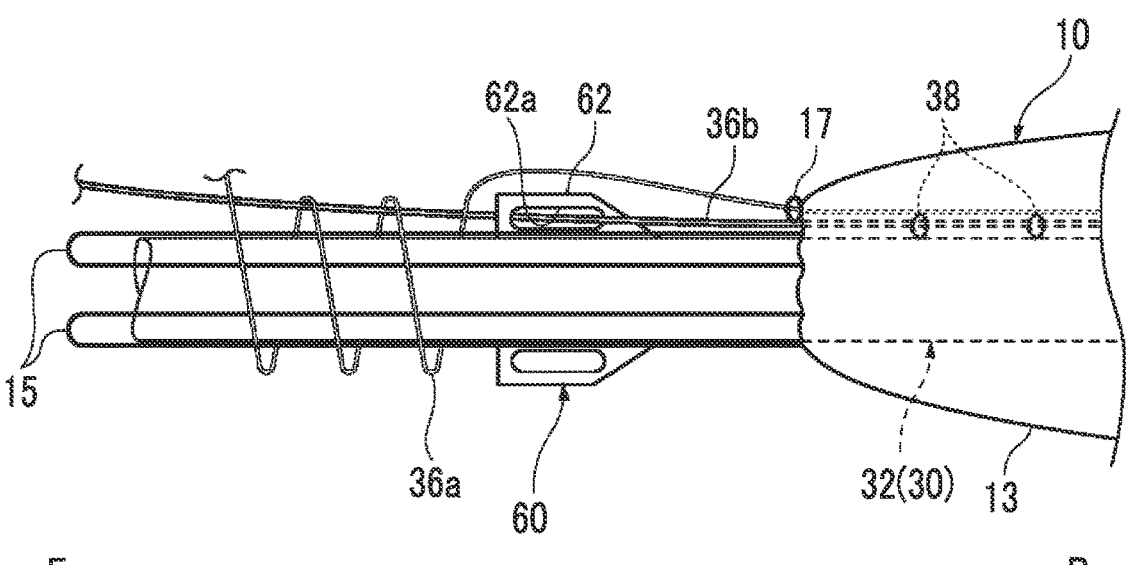
FIG. 6 is a view illustrating a disposition of first and second linear members in the second modification example.
Figure 7:
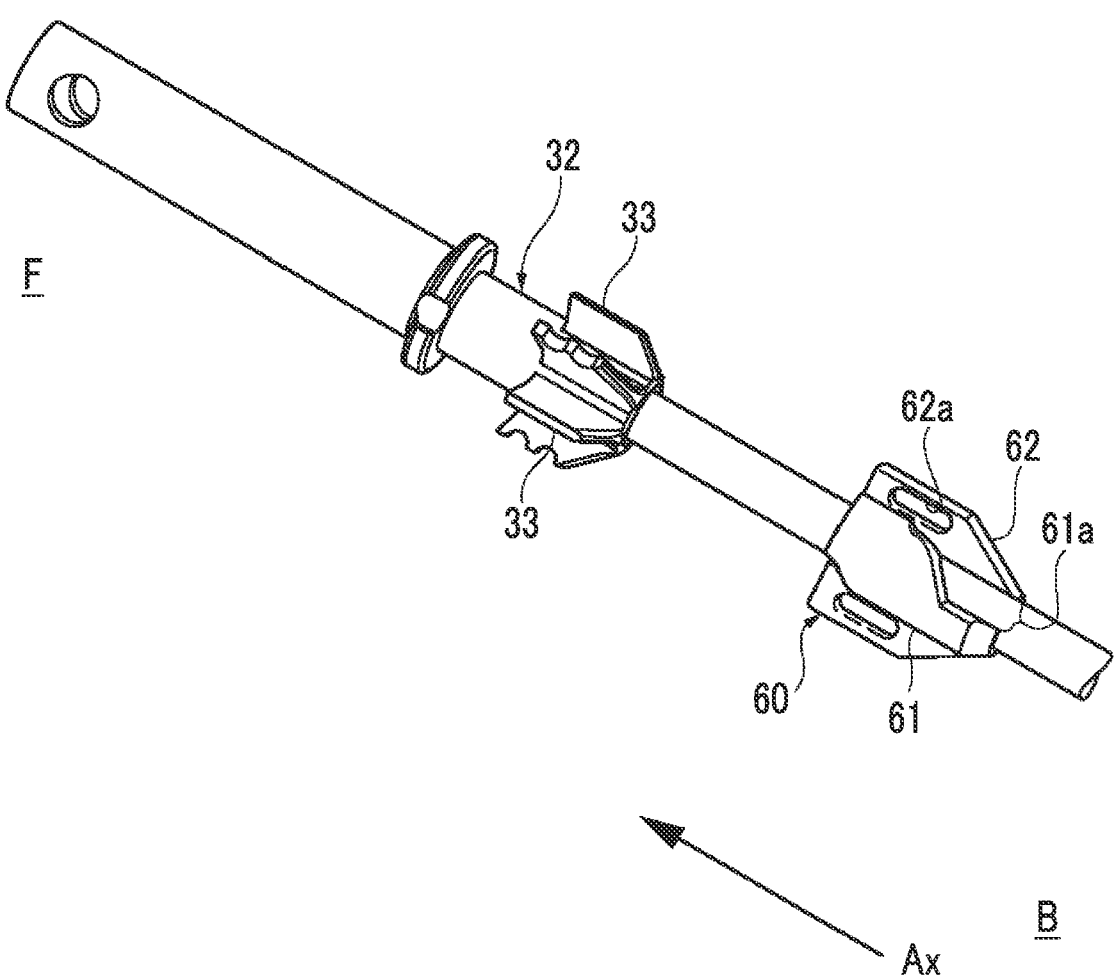
FIG. 7 is a perspective view illustrating a configuration example in the vicinity of a tip portion of the shaft small diameter portion in the second modification example.
Figure 8:
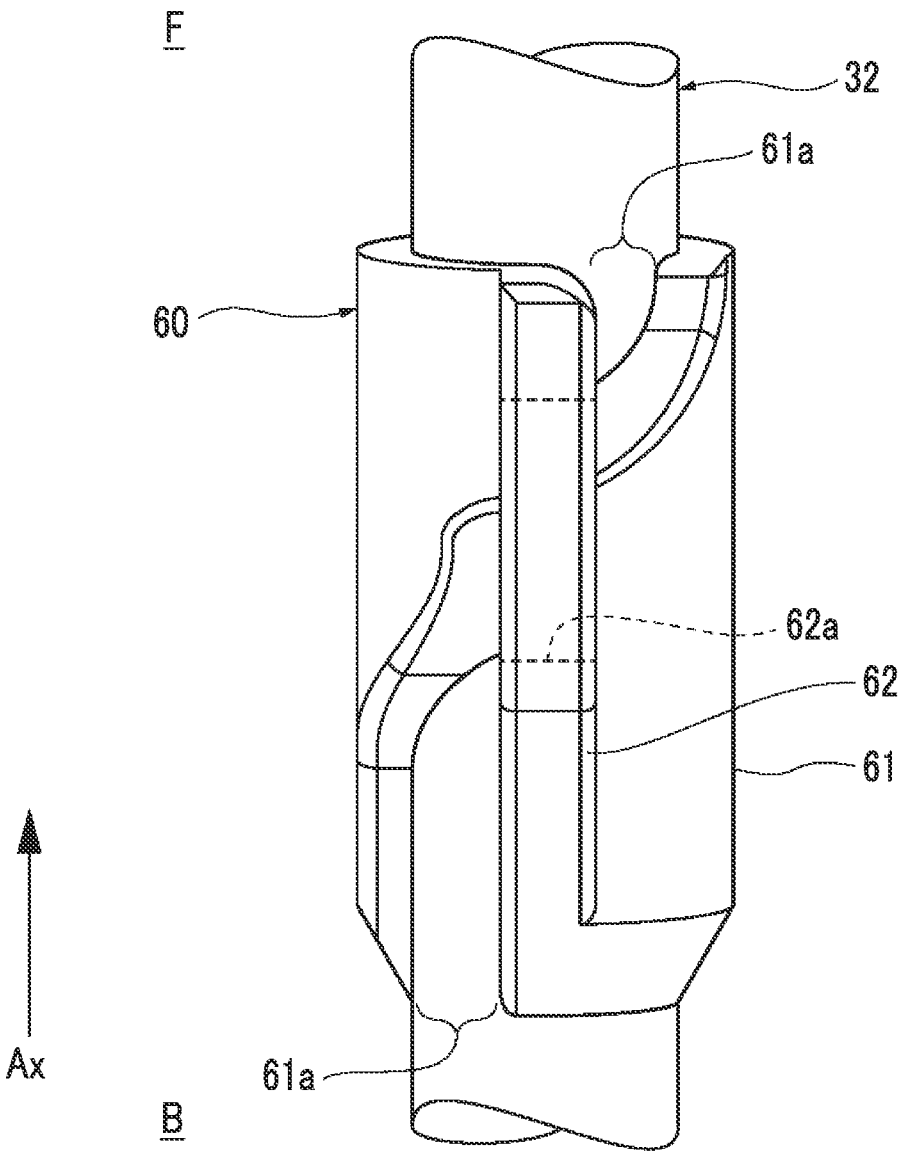
FIG. 8 is an enlarged view of a wire holder portion illustrated in FIG. 7.

FIG. 5 is a perspective view illustrating a state where the stent graft 10 is attached to the shaft small diameter portion 32 in the second modification example. FIG. 6 is a view illustrating disposition of the first and second linear members 36a and 36b in the second modification example. FIG. 7 is a perspective view illustrating a configuration example in the vicinity of the tip portion of the shaft small diameter portion 32 in the second modification example. FIG. 8 is an enlarged view of a wire holder portion 60 illustrated in FIG. 7.

As illustrated in FIG. 7, the shaft small diameter portion 32 in the second modification example has the hook piece 33 and the wire holder portion 60 which is an example of a restriction portion in this order from an end portion on one side. The wire holder portion 60 has a tubular base portion 61 attached to the shaft small diameter portion 32, and a holding piece 62 that holds the second linear member 36b. The wire holder portion 60 illustrated in FIG. 7 has two holding pieces 62 at an interval of 180 degrees.

The holding piece 62 of the wire holder portion 60 is a flat plate-shaped small piece protruding in the radial direction from the base portion 61 and extending along the axial direction Ax. A hole 62a into which the second linear member 36b is inserted in the circumferential direction is opened in the holding piece 62.

In addition, the base portion 61 of the wire holder portion 60 has a cutout portion (receiving portion) 61a that receives the second linear member 36b passing through the hole 62a of the holding piece 62. As illustrated in FIG. 8, the cutout portion 61a is cut out inward in the radial direction from a peripheral surface of the base portion 61, and is continuously formed on both sides across the holding piece 62 on the peripheral surface of the base portion 61. Then, from one side toward the other side of the base portion 61, the cutout portion 61a extends in a direction intersecting with the circumferential direction. The cutout portion 61a illustrated in FIGS. 7 and 8 has a shape in which the shaft small diameter portion 32a is exposed on a bottom surface. However, the cutout portion 61a may have a bottom formed by the base portion 61, and may be formed in a shape in which the shaft small diameter portion 32a is not exposed on the bottom surface.

In an example in FIG. 8, the cutout portion 61a is formed in a spiral shape across the holding piece 62 on the peripheral surface of the base portion 61. In this manner, in a state where the second linear member 36b passes through the hole 62a of the holding piece 62, the second linear member 36b extending in the axial direction Ax can be received in a space of the cutout portion 61a located inside the hole 62a in the radial direction.

In the second modification example, the second linear member 36b is disposed along the shaft 30 in the axial direction Ax. One side of the second linear member 36b is locked by the tip chip 35, and the other side is connected to the operating member of the hub 22 after passing through the inside of the stent graft 10. The second linear member 36b can be pulled out to the other side along the axial direction by an operation from the operating member.

In addition, as illustrated in FIGS. 5 and 6, the second linear member 36b passes through the hole 62a of the holding piece 62 of the wire holder portion 60 in the shaft small diameter portion 32. Therefore, a path of the second linear member 36b in the shaft small diameter portion 32 is defined by using the hole 62a of the holding piece 62 as a passing point.

In addition, as illustrated in FIG. 6, in the shaft 30, wire guide rings 38 into which the second linear member 36b is inserted are provided at a predetermined interval in the axial direction. The second linear member 36b is disposed along the shaft 30 by being inserted into the wire guide ring 38. In this manner, the second linear member 36b can easily follow the movement of the shaft 30 in the bent portion of the blood vessel, and the second linear member 36b can be prevented from being bent away from the shaft 30. The second linear member 36b is prevented from being bent, thereby facilitating an operation for pulling out the second linear member 36b when the stent graft 10 is released. The first linear member 36a may be inserted into the wire guide ring 38.

When the stent graft 10 is attached to the shaft small diameter portion 32, the bare portion 15 of the stent graft 10 is hooked on and engaged with the hook piece 33 of the shaft small diameter portion 32. Then, the first linear member 36a is wound in the circumferential direction from the outside of the bare portion 15 engaged with the hook piece 33 and the second linear member 36b. The diameter of the bare portion 15 is reduced, and the expansion in the radial direction is restricted. The first linear member 36a in the second modification example is wound at a position between the hook piece 33 and the wire holder portion 60 in the axial direction Ax. One end of the first linear member 36a passes through the inside of the stent graft 10, and extends to the other side of the shaft 30.

In addition, the first linear member 36a is joined to bundle the bare portion 15 via the outside of the second linear member 36b. A knot of the first linear member 36a is held to be non-detachable by engaging with the second linear member 36b. In this manner, the skeleton of the bare portion 15 can be held in a closed state. When the stent graft 10 is released, the first linear member 36a and the second linear member 36b are disengaged from each other by pulling out the second linear member 36b. Then, the knot of the first linear member 36a is untied to release the restriction on the expansion of the bare portion 15 in the radial direction by the first linear member 36a.

The knot of the first linear member 36a in the second modification example is lifted outward in the radial direction by passing through the second linear member 36b protruding in the radial direction after passing through the wire holder portion 60, and is less likely to fall into the skeleton side (inward in the radial direction). In this manner, when the stent graft 10 is released, the first linear member 36a is easily separated outward of the bare portion 15, thereby preventing an event in which the first linear member 36a is wound around the bare portion 15.

In addition, the knot of the first linear member 36a in the second modification example is fixed on one side of the wire holder portion 60 by the second linear member 36b passing through the wire holder portion 60. Therefore, the first linear member 36a is prevented from being deviated and fallen toward the wire holder portion 60 or the stent graft 10 on the other side.

In addition, the wire holder portion 60 can receive the second linear member 36*b* passing through the hole 62*a* of the holding piece 62 in the space of the cutout portion 61*a*. Therefore, the amount of the second linear member 36*b* protruding outward in the radial direction from the surface of the wire holder portion 60 can be minimized, and the bare portion 15 can be easily bundled in the radial direction in a compact manner.

In addition, in the stent graft 10, a guide ring 17 into which the first linear member 36*a* is inserted is provided in an end portion on one side of the membrane portion 13. Since the first linear member 36*a* is disposed through the guide ring 17, the movement of the first linear member 36*a* can be restricted when the stent graft 10 is released. In this manner, when the first linear member 36*a* is recovered, an event in which the first linear member 36*a* is caught on a valley portion of the skeleton can be prevented.

The present invention is not limited to the above-described embodiments, and various improvements and design changes may be made within the scope not departing from the concept of the present invention.

In the above-described embodiment, an example has been described in which the linear member 36 is held by the holding hole 34*a* of the linear member holder 34, and outward displacement of the linear member 36 in the radial direction is restricted. However, means for restricting the outward displacement of the linear member 36 in the radial direction is not limited to the configuration of the above-described embodiment. For example, the linear member 36 that winds the bare portion 15 may be fixed with a biocompatible soluble adhesive, and restraint on the bare portion 15 by the linear member 36 may be released as the adhesive exposed outward of the sheath 20 is dissolved. Here, as the above-described adhesive, for example, a medical adhesive can be adopted. In addition, for example, the above-described adhesive may be those which start to be dissolved at a temperature approximately close to a body temperature, or may be those which start to be dissolved by coming into contact with a component contained in a body fluid such as water or blood.

For example, in the above-described embodiment, an example has been described in which the stent graft 10 caused to indwell the blood vessel is used as the tubular treatment device. However, the tubular treatment device may be caused to indwell a living body lumen (for example, a digestive tract) other than the blood vessel. In addition, the tubular treatment device may be a so-called bare stent in which the skeleton portion 12 is not covered with the membrane portion 13.

In addition, the embodiments described herein are merely examples in all respects, and should be considered that the embodiments are not limited. The scope of the present invention is represented by the appended claims without being limited to the above description, and the present invention intends to include all modifications within the meaning and the scope which are equivalent to those of the appended claims.

REFERENCE SIGNS LIST

1: indwelling device
10: stent graft (tubular treatment device)
11: main body portion
12: skeleton portion
13: membrane portion
15: bare portion (engaging portion)
20: sheath

12

30: shaft
31: shaft main body portion
32: shaft small diameter portion
33: hook piece (engaged portion)
34: linear member holder (restriction portion)
34*a*: holding hole (holding portion)
36, 36*a*, 36*b*: linear member
40: guide wire
50: blood vessel (living body lumen)
51: lump
60: wire holder portion (restriction portion)
61: base portion
61*a*: cutout portion (receiving portion)
62: holding piece
62*a*: hole (holding portion)

The invention claimed is:

1. An indwelling device, comprising:
a tubular treatment device for indwelling a living body lumen, wherein the tubular treatment device is expandable in a radial direction, and has an engaging portion formed at an open end of the tubular treatment device;
a sheath capable of accommodating the tubular treatment device; and
an elongated shaft-shaped member configured to be movable forward and rearward inside the sheath along an axial direction of the sheath,
wherein the shaft-shaped member has
an engaged portion for engaging the engaging portion of the tubular treatment device, and
a restriction portion configured to restrict expansion of the engaging portion engaged with the engaged portion in the radial direction in cooperation with a linear member having at least a portion spirally wound around the engaging portion, and
the restriction portion includes a holding portion that holds the linear member, restricts displacement of the linear member held by the holding portion in the radial direction, and releases restriction on the expansion of the engaging portion in the radial direction by releasing the spirally wound portion of the linear member from around the engaging portion.

2. An indwelling device, comprising:
a tubular treatment device for indwelling a living body lumen, wherein the tubular treatment device is expandable in a radial direction, and has an engaging portion formed at an open end of the tubular treatment device,
a sheath capable of accommodating the tubular treatment device; and
an elongated shaft-shaped member configured to be movable forward and rearward inside the sheath along an axial direction of the sheath,
wherein the shaft-shaped member has
an engaged portion for engaging the engaging portion of the tubular treatment device, and
a restriction portion configured to restrict expansion of the engaging portion engaged with the engaged portion in the radial direction in cooperation with a linear member,
wherein the linear member has a first linear member having a portion wound around the engaging portion and a second linear member that holds the first linear member to be non-detachable from the engaging portion, and
the restriction portion includes a holding portion that holds the second linear member, restricts displacement of the second linear member held by the holding portion in the radial direction, restricts the expansion of the engaging portion in the radial direction by causing the first linear member and the second linear member to engage with each other, and releases the restriction by causing the first linear member and the second linear member to disengage 5 from each other by releasing the wound portion of the first linear member from around the engaging portion.

3. The indwelling device according to claim 2, wherein the second linear member is disposed in the axial 10 direction of the shaft-shaped member, and is wound by the first linear member together with the engaging portion, and the holding portion is formed to protrude outward in the radial direction from the shaft-shaped member, holds 15 the second linear member, and has a receiving portion for receiving the second linear member, the receiving portion is formed radially inward of the position where the second linear member is held.

\* \* \* \* \*      20